US008324445B2

(12) United States Patent
MacDonald et al.

(10) Patent No.: US 8,324,445 B2
(45) Date of Patent: Dec. 4, 2012

(54) COLLECTION POUCHES IN ABSORBENT ARTICLES

(75) Inventors: John Gavin MacDonald, Decatur, GA (US); Andrew Mark Long, Appleton, WI (US); Jessica Sara Van Handel, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 778 days.

(21) Appl. No.: 12/164,426

(22) Filed: Jun. 30, 2008

(65) Prior Publication Data

US 2009/0326495 A1    Dec. 31, 2009

(51) Int. Cl.
*A61F 13/15* (2006.01)

(52) U.S. Cl. .............. 604/361; 604/358; 604/385.12; 604/385.19; 604/327

(58) Field of Classification Search ............ 604/367, 604/379, 385.23, 393, 385.18, 385.12, 361, 604/327, 358
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,494,821 A | 2/1970 | Evans |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,041,203 A | 8/1977 | Brock et al. |
| 4,144,370 A | 3/1979 | Boulton |
| 4,323,534 A | 4/1982 | DesMarais |
| 4,340,563 A | 7/1982 | Appel et al. |
| 4,341,216 A | 7/1982 | Obenour |
| 4,374,888 A | 2/1983 | Bornslaeger |
| 4,535,113 A | 8/1985 | Foster et al. |
| 4,663,220 A | 5/1987 | Wisneski et al. |
| 4,704,116 A | 11/1987 | Enloe |
| 4,758,239 A | 7/1988 | Yeo et al. |
| 4,766,029 A | 8/1988 | Brock et al. |
| 4,789,592 A | 12/1988 | Taniguchi et al. |
| 4,795,668 A | 1/1989 | Krueger et al. |
| 4,798,603 A | 1/1989 | Meyer et al. |

(Continued)

FOREIGN PATENT DOCUMENTS

JP      2003052751 A     2/2003

(Continued)

OTHER PUBLICATIONS

Search Report and Written Opinion for PCT/IB2009/052012 dated Jan. 13, 2010, 11 pages.

*Primary Examiner* — Lynne Anderson
*Assistant Examiner* — Bradley Philips
(74) *Attorney, Agent, or Firm* — Dority & Manning, P.A.

(57) ABSTRACT

Absorbent articles having a pouch for the collection of bodily waste are generally disclosed. The pouch can generally be located on or within the wearer contacting surface of an absorbent article. The pouch can have an opening ready to receive the bodily waste or can include a pouch opening mechanism. Additionally, a pouch closing mechanism can be included within the absorbent article to close the opening of the pouch upon collection of the bodily waste.

20 Claims, 9 Drawing Sheets

U.S. PATENT DOCUMENTS

| | | | |
|---|---|---|---|
| 4,801,494 A | 1/1989 | Datta et al. | |
| 4,834,738 A | 5/1989 | Kielpikowski et al. | |
| 4,908,026 A | 3/1990 | Sukiennik et al. | |
| 5,048,589 A | 9/1991 | Cook et al. | |
| 5,057,368 A | 10/1991 | Largman et al. | |
| 5,069,970 A | 12/1991 | Largman et al. | |
| 5,093,422 A | 3/1992 | Himes | |
| 5,108,820 A | 4/1992 | Kaneko et al. | |
| 5,162,074 A | 11/1992 | Hills | |
| 5,169,706 A | 12/1992 | Collier, IV et al. | |
| 5,176,668 A | 1/1993 | Bernardin | |
| 5,176,672 A | 1/1993 | Bruemmer et al. | |
| 5,192,606 A | 3/1993 | Proxmire et al. | |
| 5,213,881 A | 5/1993 | Timmons et al. | |
| 5,248,309 A | 9/1993 | Serbiak et al. | |
| 5,273,236 A | 12/1993 | Wootton et al. | |
| 5,277,976 A | 1/1994 | Hogle et al. | |
| 5,278,272 A | 1/1994 | Lai et al. | |
| 5,284,703 A | 2/1994 | Everhart et al. | |
| 5,290,628 A | 3/1994 | Lim et al. | |
| 5,304,599 A | 4/1994 | Himes | |
| 5,332,613 A | 7/1994 | Taylor et al. | |
| 5,336,552 A | 8/1994 | Strack et al. | |
| 5,382,400 A | 1/1995 | Pike et al. | |
| 5,399,412 A | 3/1995 | Sudall et al. | |
| 5,415,644 A * | 5/1995 | Enloe | 604/385.19 |
| 5,464,688 A | 11/1995 | Timmons et al. | |
| 5,466,410 A | 11/1995 | Hills | |
| 5,486,166 A | 1/1996 | Bishop et al. | |
| 5,490,846 A | 2/1996 | Ellis et al. | |
| 5,509,915 A | 4/1996 | Hanson et al. | |
| 5,539,056 A | 7/1996 | Yang et al. | |
| 5,596,052 A | 1/1997 | Resconi et al. | |
| 5,628,737 A | 5/1997 | Dobrin et al. | |
| 5,647,863 A | 7/1997 | Hammons et al. | |
| 5,672,248 A | 9/1997 | Wendt et al. | |
| 5,693,385 A | 12/1997 | Parks | |
| 5,766,213 A * | 6/1998 | Hackman et al. | 604/385.01 |
| 5,834,114 A | 11/1998 | Economy et al. | |
| 5,836,932 A | 11/1998 | Buell et al. | |
| 5,843,057 A | 12/1998 | McCormack | |
| 5,849,002 A | 12/1998 | Carlos et al. | |
| 5,855,999 A | 1/1999 | McCormack | |
| 5,865,824 A | 2/1999 | Chen et al. | |
| 5,895,379 A | 4/1999 | Litchholt et al. | |
| 5,932,497 A | 8/1999 | Morman et al. | |
| 5,997,981 A | 12/1999 | McCormack et al. | |
| 6,002,064 A | 12/1999 | Kobylivker et al. | |
| 6,015,764 A | 1/2000 | McCormack et al. | |
| 6,037,281 A | 3/2000 | Mathis et al. | |
| 6,111,163 A | 8/2000 | McCormack et al. | |
| 6,114,024 A | 9/2000 | Forte | |
| 6,133,501 A | 10/2000 | Hallock et al. | |
| 6,149,934 A | 11/2000 | Krzysik et al. | |
| 6,153,209 A | 11/2000 | Vega et al. | |
| 6,171,291 B1 | 1/2001 | Osborn, III et al. | |
| 6,198,018 B1 | 3/2001 | Curro | |
| 6,200,669 B1 | 3/2001 | Marmon et al. | |
| 6,203,810 B1 | 3/2001 | Alemany et al. | |
| 6,245,401 B1 | 6/2001 | Ying et al. | |
| 6,293,933 B1 | 9/2001 | Ahlstrand | |
| 6,315,864 B2 | 11/2001 | Anderson et al. | |
| 6,346,097 B1 * | 2/2002 | Blaney | 604/327 |
| 6,420,626 B1 | 7/2002 | Erspamer et al. | |
| 6,423,044 B1 * | 7/2002 | Roe et al. | 604/385.12 |
| 6,423,045 B1 * | 7/2002 | Wise et al. | 604/385.12 |
| 6,429,351 B1 | 8/2002 | Giodotti et al. | |
| 6,461,457 B1 | 10/2002 | Taylor et al. | |
| 6,517,906 B1 | 2/2003 | Economy et al. | |
| 6,527,756 B1 | 3/2003 | Mishima et al. | |
| 6,573,212 B2 | 6/2003 | McCrae et al. | |
| 6,639,004 B2 | 10/2003 | Falat et al. | |
| 6,642,427 B2 | 11/2003 | Roe et al. | |
| 6,660,903 B1 | 12/2003 | Chen et al. | |
| 6,663,611 B2 | 12/2003 | Blaney et al. | |
| 6,677,498 B2 | 1/2004 | Chen et al. | |
| 6,702,796 B2 | 3/2004 | McFall et al. | |
| 6,794,024 B1 | 9/2004 | Walton et al. | |
| 6,929,819 B2 | 8/2005 | Underhill et al. | |
| 6,932,800 B2 | 8/2005 | LaVon et al. | |
| 6,958,430 B1 | 10/2005 | Marinelli | |
| 7,002,055 B2 | 2/2006 | Long et al. | |
| 7,156,830 B2 | 1/2007 | Koyama et al. | |
| 7,156,832 B2 | 1/2007 | Drevik et al. | |
| 7,250,548 B2 | 7/2007 | Weber et al. | |
| 7,297,835 B2 | 11/2007 | Olson | |
| 2003/0120253 A1 | 6/2003 | Wentzel et al. | |
| 2003/0125682 A1 | 7/2003 | Olson et al. | |
| 2003/0187418 A1 | 10/2003 | Kudo et al. | |
| 2004/0166248 A1 | 8/2004 | Hu et al. | |
| 2004/0254549 A1 | 12/2004 | Olson et al. | |
| 2005/0203473 A1 | 9/2005 | Pesce et al. | |
| 2006/0047257 A1 | 3/2006 | Raidel | |
| 2006/0142713 A1 | 6/2006 | Long et al. | |
| 2006/0142714 A1 | 6/2006 | Jackson et al. | |
| 2006/0142715 A1 | 6/2006 | Long et al. | |
| 2006/0142716 A1 | 6/2006 | Long et al. | |
| 2006/0293632 A1 | 12/2006 | Long et al. | |
| 2007/0173160 A1 | 7/2007 | Lee | |
| 2008/0269703 A1 | 10/2008 | Collins et al. | |
| 2009/0157022 A1 | 6/2009 | MacDonald et al. | |
| 2009/0157032 A1 | 6/2009 | MacDonald et al. | |
| 2009/0240220 A1 | 9/2009 | MacDonald et al. | |
| 2009/0299312 A1 | 12/2009 | MacDonald et al. | |

FOREIGN PATENT DOCUMENTS

| | | |
|---|---|---|
| KR | 20035756 Y1 | 7/2004 |
| WO | WO 9619172 A1 | 6/1996 |
| WO | WO 0241817 A1 | 5/2002 |
| WO | WO 02091968 A2 | 11/2002 |
| WO | WO 02091968 A3 | 11/2002 |
| WO | WO 2004082448 A1 | 9/2004 |

* cited by examiner

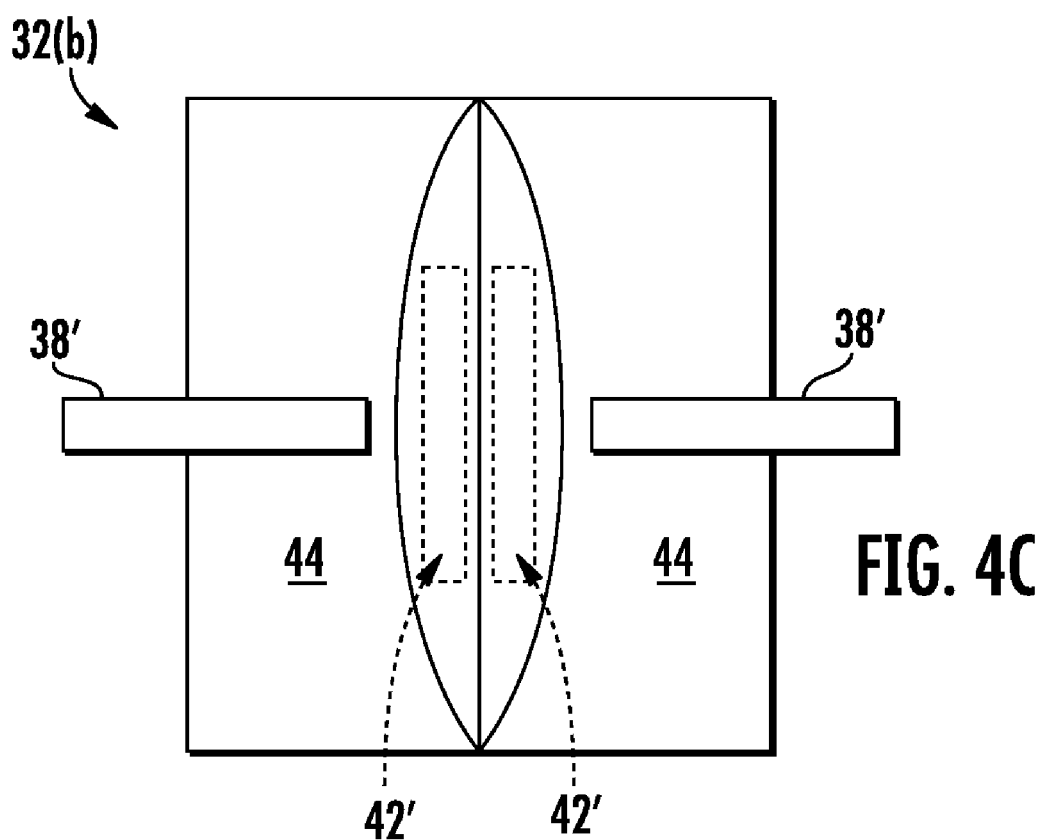

COLLECTION POUCHES IN ABSORBENT ARTICLES

BACKGROUND OF THE INVENTION

Absorbent articles, such as diapers, training pants, incontinence articles, etc, are designed to be worn by the wearer and absorb urine and other bodily fluids released by the wearer. However, in conventional absorbent articles, soft, runny fecal matter tends to sit on the topsheet adjacent to the wearer's skin without being absorbed into the absorbent core of the absorbent article. The solid matter included in this soft, runny fecal matter inhibits its passage into the absorbent core. However, having fecal matter sit adjacent to the skin of the wearer can create a sanitary or health issue for the wearer.

As such a need exists to reduce the amount of fecal matter that contacts the skin of the wearer.

SUMMARY OF THE INVENTION

Objects and advantages of the invention will be set forth in part in the following description, or may be understood from the description, or may be learned through practice of the invention.

In one embodiment, the present invention is generally directed to an absorbent article including a liquid-permeable body-side liner, a liquid-impermeable outer cover, an absorbent core positioned between the liquid-permeable body-side liner and the liquid-impermeable outer cover, and a pouch positioned between the liquid-permeable body-side liner and the absorbent core. The pouch can be configured to collect and retain bodily waste through an opening facing the liquid-permeable body-side liner. A closing mechanism, including at least one compressed substrate, can be positioned adjacent the pouch such that upon contact with a liquid, the compressed substrate expands to close the pouch.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which:

FIGS. 4A-4C sequentially show the process of FIGS. 3A-3C of a pouch opening upon wetting, collecting fecal matter, and then closing upon collection of the fecal matter in an absorbent article from a top view;

Figure 1:
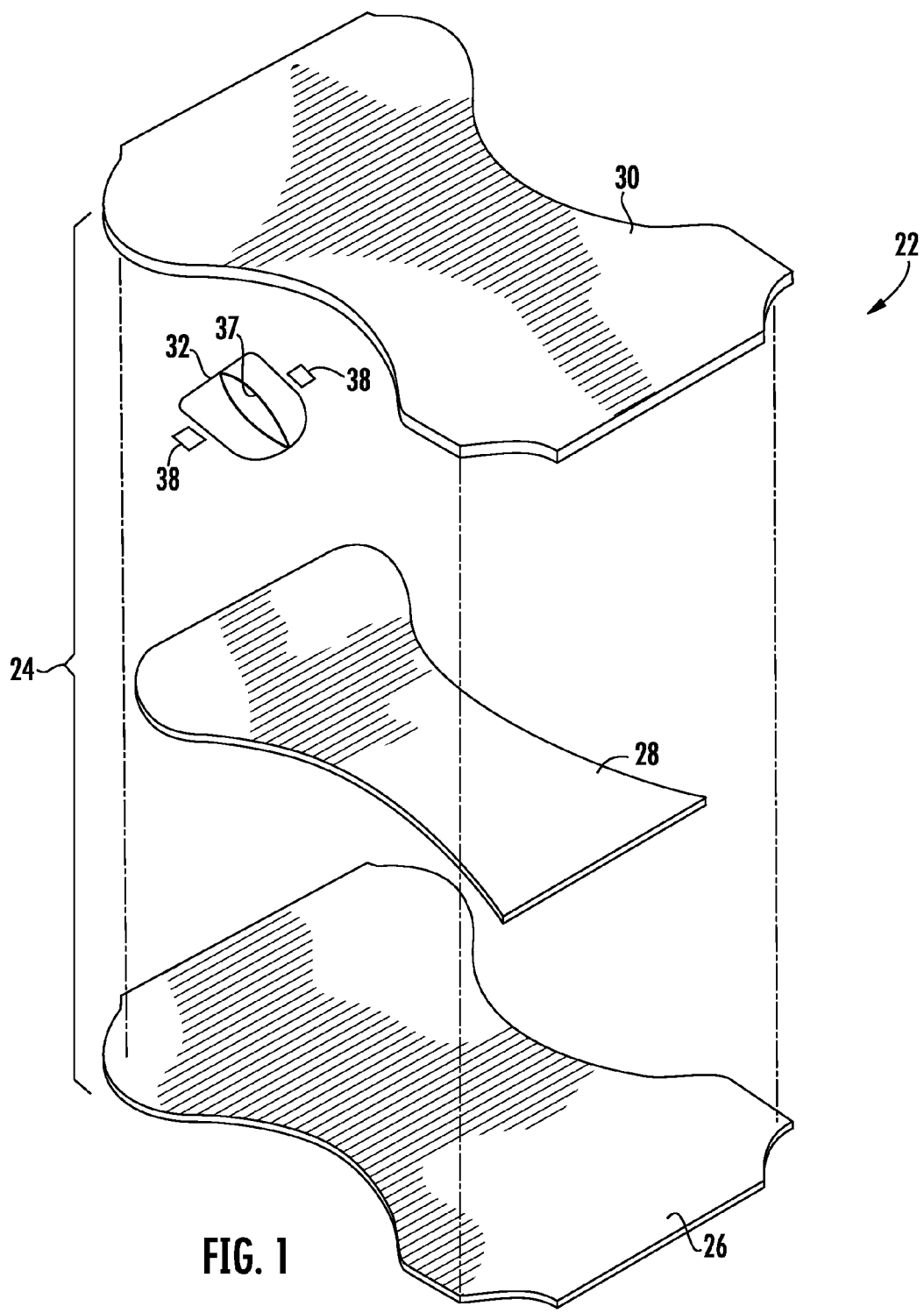
FIG. 1 shows the construction of an exemplary diaper having a pouch for collection of fecal matter.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

In general, the present disclosure is directed to absorbent articles having a pouch for the collection of bodily fluids, particularly fecal matter. The presently disclosed pouches are particularly suitable for the collection of soft, runny fecal matter that has a significant amount of bodily fluid mixed with the solid fecal matter. Thus, fecal matter can be collected into the pouch and retained within the pouch helping inhibit contact with the skin of the wearer.

The pouch can generally be located on or within the wearer contacting surface of an absorbent article (e.g., a diaper, incontinence article, training pant, etc.). In one embodiment, the pouch can be located in the back end of the crotch wear the anus of the wearer is located when donned, so as to be positioned for collection of feces. In this embodiment, the pouch is particularly preferred to not extend into the front portion of the crotch to allow any urine released from the wearer to pass through the topsheet of the absorbent article and into the absorbent core without impedance from the pouch.

For purposes of illustration only, an absorbent article is shown in FIG. 1 as a diaper 22. In the illustrated embodiment, the diaper 22 is shown as having an hourglass shape in an unfastened configuration. However, other shapes may of course be utilized, such as a generally rectangular shape, T-shape, or I-shape. As shown, the diaper 22 includes a chassis 24 formed by various components, including an outer cover 26, body-side liner 30, absorbent core 28.

The body-side liner 30 is generally employed to help isolate the wearer's skin from liquids held in the absorbent core 28. For example, the liner 30 presents a bodyfacing surface that is typically compliant, soft feeling, and non-irritating to the wearer's skin. Typically, the liner 30 is also less hydrophilic than the absorbent core 28 so that its surface remains relatively dry to the wearer. The liner 30 may be liquid-permeable to permit liquid to readily penetrate through its thickness. The body-side liner 30 may be formed from a wide variety of materials, such as porous foams, reticulated foams, apertured plastic films, natural fibers (e.g., wood or cotton fibers), synthetic fibers (e.g., polyethylene or polypropylene fibers), or a combination thereof. In some embodiments, woven and/or nonwoven fabrics are used for the liner 30. For example, the body-side liner 30 may be formed from a melt-blown or spunbonded web of polyolefin fibers. The liner 30 may also be a bonded-carded web of natural and/or synthetic fibers. The liner 30 may further be composed of a substantially hydrophobic material that is optionally treated with a surfactant or otherwise processed to impart a desired level of wettability and hydrophilicity. The surfactant may be applied by any conventional method, such as spraying, printing, brush coating, foaming, and so forth. When utilized, the surfactant may be applied to the entire liner 30 or may be selectively applied to particular sections of the liner 30, such as to the medial section along the longitudinal centerline of the diaper. The liner 30 may further include a composition that is configured to transfer to the wearer's skin for improving skin health. Suitable compositions for use on the liner 30 are described in U.S. Pat. No. 6,149,934 to Krzvsik et al., which is incorporated herein in its entirety by reference thereto for all purposes.

Additionally, the body-side liner 30 of the absorbent article can hold the pouch in place within the absorbent article. In one embodiment, the body-side liner 30 can be more porous than the body-side liners conventionally used in the construction of absorbent articles. Effectively, the pores of the relatively porous body-side liner 30 can allow liquid, as well as soft, runny fecal matter, to easily pass through the porous body-side liner 30.

The outer cover 26 is typically formed from a material that is substantially impermeable to liquids. For example, the outer cover 26 may be formed from a thin plastic film or other flexible liquid-impermeable material. In one embodiment, the outer cover 26 is formed from a polyethylene film having a thickness of from about 0.01 millimeter to about 0.05 millimeter. If a more cloth-like feeling is desired, the outer cover 26 may be formed from a polyolefin film laminated to a nonwoven web. For example, a stretch-thinned polypropylene film having a thickness of about 0.015 millimeter may be thermally laminated to a spunbond web of polypropylene fibers. The polypropylene fibers may have a denier per filament of about 1.5 to 2.5, and the nonwoven web may have a basis weight of about 17 grams per square meter. The outer cover 26 may also include bicomponent fibers, such as polyethylene/polypropylene bicomponent fibers. In addition, the outer cover 26 may also contain a material that is impermeable to liquids, but permeable to gases and water vapor (i.e., "breathable"). This permits vapors to escape from the absorbent core 28, but still prevents liquid exudates from passing through the outer cover 26.

It should be understood, however, that other layers may also be included in the diaper 22 shown in FIG. 1 in accordance with the present invention. Likewise, one or more of the layers referred to in FIG. 1 may also be eliminated in certain embodiments of the present invention.

For example, a surge layer (not shown) can be present to help to decelerate and diffuse surges or gushes of liquid that may be rapidly introduced into the absorbent core 28. Desirably, the surge layer rapidly accepts and temporarily holds the liquid prior to releasing it into the storage or retention portions of the absorbent core 28. For example, the surge layer can be interposed between an inwardly facing surface of the body-side liner 30 and the absorbent core 28. Alternatively, the surge layer may be located on an outwardly facing surface of the body-side liner 30. The surge layer is typically constructed from highly liquid-permeable materials. Suitable materials may include porous woven materials, porous nonwoven materials, and apertured films. Some examples include, without limitation, flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. Other examples of suitable surge layers 32 are described in U.S. Pat. No. 5,486,166 to Ellis et al. and U.S. Pat. No. 5,490,846 to Ellis, et al., which are incorporated by reference herein.

Besides the above-mentioned components, the diaper 22 may also contain various other components as is known in the art. For example, the diaper 22 may also contain a substantially hydrophilic tissue wrapsheet (not illustrated) that helps maintain the integrity of the fibrous structure of the absorbent core 28. The tissue wrapsheet is typically placed about the absorbent core 28 over at least the two major facing surfaces thereof, and composed of an absorbent cellulosic material, such as creped wadding or a high wet-strength tissue. The tissue wrapsheet may be configured to provide a wicking layer that helps to rapidly distribute liquid over the mass of absorbent fibers of the absorbent core 28. The wrapsheet material on one side of the absorbent fibrous mass may be bonded to the wrapsheet located on the opposite side of the fibrous mass to effectively entrap the absorbent core 28.

Furthermore, the diaper 22 may also include a ventilation layer (not shown) that is positioned between the absorbent core 28 and the outer cover 26. When utilized, the ventilation layer may help insulate the outer cover 26 from the absorbent core 28, thereby reducing dampness in the outer cover 26. Examples of such ventilation layers may include breathable laminates (e.g., nonwoven web laminated to a breathable film), such as described in U.S. Pat. No. 6,663,611 to Blaney, et al., which is incorporated herein in its entirety by reference thereto for all purpose.

The diaper 22 may also include a pair of containment flaps that are configured to provide a barrier and to contain the lateral flow of body exudates. The containment flaps may be located along the laterally opposed side edges of the body-side liner adjacent the side edges of the absorbent core. The containment flaps may extend longitudinally along the entire length of the absorbent core 28, or may only extend partially along the length of the absorbent core 28. When the containment flaps are shorter in length than the absorbent core 28, they may be selectively positioned anywhere along the side edges of diaper 22 in the crotch region. In one embodiment, the containment flaps extend along the entire length of the absorbent core 28 to better contain the body exudates. Such containment flaps are generally well known to those skilled in the art. For example, suitable constructions and arrangements for the containment flaps are described in U.S. Pat. No. 4,704,116 to Enloe, which is incorporated by reference herein.

The diaper 22 may include various elastic or stretchable materials, such as a pair of leg elastic members affixed to the side edges to further prevent leakage of body exudates and to support the absorbent core 28. In addition, a pair of waist elastic members may be affixed to longitudinally opposed waist edges of the diaper 22. The leg elastic members and the waist elastic members are generally adapted to closely fit about the legs and waist of the wearer in use to maintain a positive, contacting relationship with the wearer and to effectively reduce or eliminate the leakage of body exudates from the diaper 22. As used herein, the terms "elastic" and "stretchable" include any material that may be stretched and return to its original shape when relaxed. Suitable polymers for forming such materials include, but are not limited to, block copolymers of polystyrene, polyisoprene and polybutadiene; copolymers of ethylene, natural rubbers and urethanes; etc. Particularly suitable are styrene-butadiene block copolymers sold by Kraton Polymers of Houston, Tex. under the trade name Kraton®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Also suitable are coextruded composites of the foregoing, and elastomeric staple integrated composites where staple fibers of polypropylene, polyester, cotton and other materials are integrated into an elastomeric meltblown web. Certain elastomeric single-site or metallocene-catalyzed olefin polymers and copolymers are also suitable for the side panels.

The diaper 22 may also include one or more fasteners. For example, two flexible fasteners can be present on opposite side edges of waist regions to create a waist opening and a pair of leg openings about the wearer. The shape of the fasteners may generally vary, but may include, for instance, generally rectangular shapes, square shapes, circular shapes, triangular shapes, oval shapes, linear shapes, and so forth. The fasteners may include, for instance, a hook material. In one particular embodiment, each fastener includes a separate piece of hook material affixed to the inside surface of a flexible backing.

The various regions and/or components of the diaper 22 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the outer cover 26 and body-side liner 30 are assembled to each other and to the absorbent core 28 using an adhesive. Alternatively, the absorbent core 28 may be connected to the outer cover 26 using conventional fasteners, such as buttons, hook and loop type fasteners, adhesive tape fasteners, and so forth. Similarly, other diaper components, such as the leg elastic members, waist elastic members and fasteners, may also be assembled into the diaper 22 using any attachment mechanism.

Although various configurations of a diaper have been described above, it should be understood that other diaper and absorbent article configurations are also included within the scope of the present invention. For instance, other suitable diaper configurations are described in U.S. Pat. No. 4,798,603 to Meyer et al.; U.S. Pat. No. 5,176,668 to Bemardin; U.S. Pat. No. 5,176,672 to Bruemmer et al.; U.S. Pat. No. 5,192,606 to Proxmire et al.; and U.S. Pat. No. 5,509,915 to Hanson et al., as well as U.S. Patent Application Pub. No. 2003/120253 to Wentzel, et al., all of which are incorporated herein in their entirety by reference thereto for all purposes.

I. Pouch

In the embodiment shown in FIG. 1, a pouch 32 for the collection of bodily fluids, particularly fecal matter is located between the body-side liner 30 and the absorbent core 28. Thus, fecal matter can be collected into the pouch 32 and retained within the pouch 32 helping inhibit contact with the skin of the wearer.

The pouch is constructed from a liquid impermeable sheet (e.g., a film) that is flexible and liquid impermeable. As such, the pouch can retain any liquid or solid located within the pouch and substantially prevent the liquid or solid from passing through the pouch walls. For example, the liquid impermeable sheet of the pouch may be formed from a thin plastic film or other flexible liquid-impermeable material. In one embodiment, the liquid impermeable sheet of the pouch is formed from a polyethylene film, which can have a thickness of from about 0.01 millimeter to about 0.05 millimeter.

In addition, the liquid impermeable sheet of the pouch may also contain a material that is impermeable to liquids, but permeable to gases and water vapor (i.e., "breathable"). This permits vapors to escape from the pouch, but still prevents liquid exudates from passing through the pouch. As used herein, the term "breathable" means pervious to water vapor and gases, but impermeable to liquid water. For instance, "breathable barriers" and "breathable films" allow water vapor to pass therethrough, but are substantially impervious to liquid water. The "breathability" of a material is measured in terms of water vapor transmission rate (WVTR), with higher values representing a more vapor-pervious material and lower values representing a less vapor-pervious material. Typically, the "breathable" materials have a water vapor transmission rate (WVTR) of from about 500 to about 20,000 grams per square meter per 24 hours ($g/m^2/24$ hours), in some embodiments from about 1,000 to about 15,000 $g/m^2/24$ hours, and in some embodiments, from about 1,500 to about 14,000 $g/m^2/24$ hours.

The film layer of the laminate is typically formed from a material that is substantially impermeable to liquids. For example, the film layer may be formed from a thin plastic film or other flexible liquid-impermeable material. In one embodiment, the film layer is formed from a polyethylene film having a thickness of from about 0.01 millimeter to about 0.05 millimeter. For example, a stretch-thinned polypropylene film having a thickness of about 0.015 millimeter may be thermally laminated to the nonwoven web.

In addition, the film layer may be formed from a material that is impermeable to liquids, but permeable to gases and water vapor (i.e., "breathable"). This permits vapors to pass through the laminate, but still prevents liquid exudates from passing through the laminate. The use of a breathable laminate is especially advantageous when the laminate is used as an outercover of an absorbent article to permit vapors to escape from the absorbent core, but still prevents liquid exudates from passing through the outer cover. For example, the breathable film may be a microporous or monolithic film.

The film may be formed from a polyolefin polymer, such as linear, low-density polyethylene (LLDPE) or polypropylene. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers.

If desired, the breathable film may also contain an elastomeric polymer, such as elastomeric polyesters, elastomeric polyurethanes, elastomeric polyamides, elastomeric polyolefins, elastomeric copolymers, and so forth. Examples of elastomeric copolymers include block copolymers having the general formula A-B-A' or A-B, wherein A and A' are each a thermoplastic polymer endblock that contains a styrenic moiety (e.g., poly(vinyl arene)) and wherein B is an elastomeric polymer midblock, such as a conjugated diene or a lower alkene polymer (e.g., polystyrene-poly(ethylene-butylene)-polystyrene block copolymers). Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer. Commercially available A-B-A' and A-B-A-B copolymers include several different formulations from Kraton Polymers of Houston, Tex. under the trade designation KRATON®. KRATON® block copolymers are available in several different formulations, a number of which are identified in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S or styrene-poly(ethylene-propylene)-styrene elastomeric copolymer available from Kuraray Company, Ltd. of Okayama, Japan, under the trade name SEPTON®.

Examples of elastomeric polyolefins include ultra-low density elastomeric polypropylenes and polyethylenes, such as those produced by "single-site" or "metallocene" catalysis methods. Such elastomeric olefin polymers are commercially available from ExxonMobil Chemical Co. of Houston, Tex. under the trade designations ACHIEVE® (propylene-based), EXACT® (ethylene-based), and EXCEED® (ethylene-based). Elastomeric olefin polymers are also commercially available from DuPont Dow Elastomers, LLC (a joint venture between DuPont and the Dow Chemical Co.) under the trade designation ENGAGE® (ethylene-based) and AFFINITY® (ethylene-based). Examples of such polymers are also described in U.S. Pat. Nos. 5,278,272 and 5,272,236 to Lai, et al., which are incorporated herein in their entirety by reference thereto for all purposes. Also useful are certain elastomeric polypropylenes, such as described in U.S. Pat. No. 5,539,056 to Yang, et al. and U.S. Pat. No. 5,596,052 to Resconi, et al., which are incorporated herein in their entirety by reference thereto for all purposes.

If desired, blends of two or more polymers may also be utilized to form the breathable film. For example, the film may be formed from a blend of a high performance elastomer and a lower performance elastomer. A high performance elastomer is generally an elastomer having a low level of hysteresis, such as less than about 75%, and in some embodiments, less than about 60%. Likewise, a low performance elastomer is generally an elastomer having a high level of hysteresis, such as greater than about 75%. The hysteresis value may be determined by first elongating a sample to an ultimate elongation of 50% and then allowing the sample to retract to an amount where the amount of resistance is zero. Particularly suitable high performance elastomers may include styrenic-based block copolymers, such as described above and commercially available from Kraton Polymers of Houston, Tex. under the trade designation KRATON®. Likewise, particularly suitable low performance elastomers include elastomeric polyolefins, such as metallocene-catalyzed polyolefins (e.g., single site metallocene-catalyzed linear low density polyethylene) commercially available from DuPont Dow Elastomers, LLC under the trade designation AFFINITY®. In some embodiments, the high performance elastomer may constitute from about 25 wt. % to about 90 wt. % of the polymer component of the film, and the low performance elastomer may likewise constitute from about 10 wt. % to about 75 wt. % of the polymer component of the film. Further examples of such a high performance/low performance elastomer blend are described in U.S. Pat. No. 6,794,024 to Walton, et al., which is incorporated herein in its entirety by reference thereto for all purposes.

As stated, the breathable film may be microporous. The micropores form what is often referred to as tortuous pathways through the film. Liquid contacting one side of the film does not have a direct passage through the film. Instead, a network of microporous channels in the film prevents liquids from passing, but allows gases and water vapor to pass. Microporous films may be formed from a polymer and a filler (e.g., calcium carbonate). Fillers are particulates or other forms of material that may be added to the film polymer extrusion blend and that will not chemically interfere with the extruded film, but which may be uniformly dispersed throughout the film. Generally, on a dry weight basis, based on the total weight of the film, the film includes from about 30% to about 90% by weight of a polymer. In some embodiments, the film includes from about 30% to about 90% by weight of a filler. Examples of such films are described in U.S. Pat. No. 5,843,057 to McCormack; U.S. Pat. No. 5,855,999 to McCormack; U.S. Pat. No. 5,932,497 to Morman, et al.; U.S. Pat. No. 5,997,981 to McCormack et al.; U.S. Pat. No. 6,002,064 to Kobylivker, et al.; U.S. Pat. No. 6,015,764 to McCormack, et al.; U.S. Pat. No. 6,037,281 to Mathis, et al.; U.S. Pat. No. 6,111,163 to McCormack, et al.; and U.S. Pat. No. 6,461,457 to Taylor, et al., which are incorporated herein in their entirety by reference thereto for all purposes.

The films are generally made breathable by stretching the filled films to create the microporous passageways as the polymer breaks away from the filler (e.g., calcium carbonate) during stretching. For example, the breathable material contains a stretch-thinned film that includes at least two basic components, i.e., a polyolefin polymer and filler. These components are mixed together, heated, and then extruded into a film layer using any one of a variety of film-producing processes known to those of ordinary skill in the film processing art. Such film-making processes include, for example, cast embossed, chill and flat cast, and blown film processes.

Another type of breathable film is a monolithic film that is a nonporous, continuous film, which because of its molecular structure, is capable of forming a liquid-impermeable, vapor-permeable barrier. Among the various polymeric films that fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. Without intending to be held to a particular mechanism of operation, it is believed that films made from such polymers solubilize water molecules and allow transportation of those molecules from one surface of the film to the other. Accordingly, these films may be sufficiently continuous, i.e., nonporous, to make them substantially liquid-impermeable, but still allow for vapor permeability.

Breathable films, such as described above, may constitute the entire breathable material, or may be part of a multilayer film. Multilayer films may be prepared by cast or blown film coextrusion of the layers, by extrusion coating, or by any conventional layering process. Further, other breathable materials that may be suitable for use in the present invention are described in U.S. Pat. No. 4,341,216 to Obenour; U.S. Pat. No. 4,758,239 to Yeo, et al.; U.S. Pat. No. 5,628,737 to Dobrin, et al.; U.S. Pat. No. 5,836,932 to Buell; U.S. Pat. No. 6,114,024 to Forte; U.S. Pat. No. 6,153,209 to Vega, et al.; U.S. Pat. No. 6,198,018 to Curro; U.S. Pat. No. 6,203,810 to Alemany, et al.; and U.S. Pat. No. 6,245,401 to Ying, et al., which are incorporated herein in their entirety by reference thereto for all purposes.

The pouch 32 can take on any shape or configuration that enables the pouch to collect and substantially retain liquid and/or feces passing through the body-side liner 30. For example, the pouch 32 can be provided in an open configuration that allows for the collection of the bodily fluid immediately or can be provided in a more closed configuration that opens upon contact with the bodily fluid. Exemplary embodiments of these configurations are provided in greater detail below.

A. Open Pouch

In one embodiment, the pouch can be open in the absorbent article prior to donning by the wearer. In this embodiment, the pouch is already open and ready to receive bodily fluids from the wearer. Additionally, the pouch can be configured such that the collection space within the pouch expands as bodily fluids are collected.

Figure 2A:
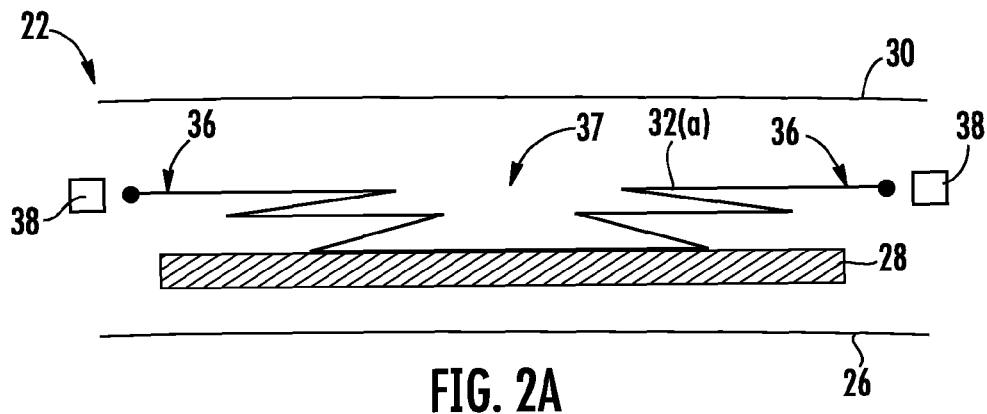
FIGS. 2A-2C sequentially show a process of an open pouch collecting and closing upon collection of the fecal matter in an absorbent article.

For example, referring to FIG. 2A, the pouch 32(a) is shown positioned between the body-side liner 30 and the absorbent core 28 of the diaper 22. The pouch 32(a) is shown folded in a zig-zag manner along each of its side edges 36. Specifically, each side is folded upon itself at least twice to create an accordion-shaped fold along each side, such as at least 4 accordion-shaped folds. In one particular embodiment, each side can be folded from about 4 accordion-shaped folds to about 20 accordion-shaped folds. The accordion-shaped folds allows the pouch to remain substantially flat while folded within the construction of the absorbent article. As such, the pouch 32(a) lays substantially flat within the layers of the diaper 22 prior to insult with a bodily fluid.

Figure 2B:
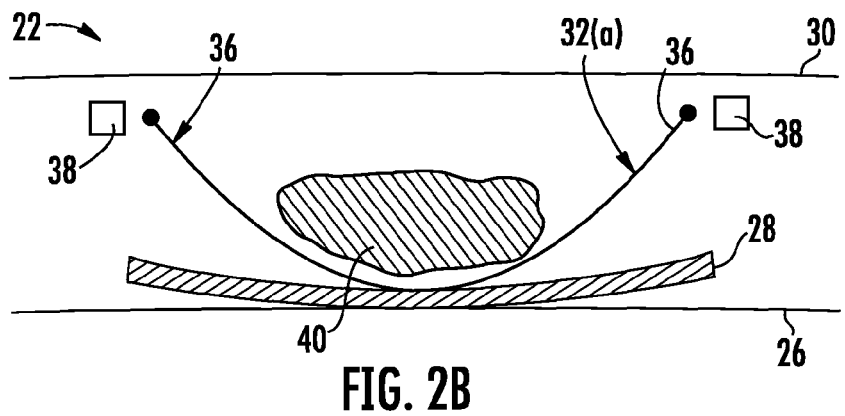
Figure 2C:
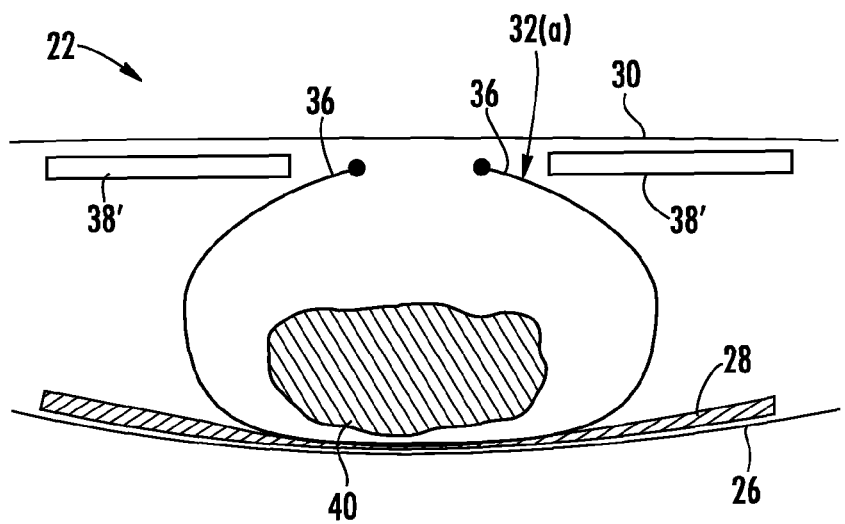

Upon insult with a bodily fluid and/or feces, the bodily fluid enters the opening 37 formed by the walls of the pouch 32(a) and expands the area defined by the pouch 32(a). The bodily waste, through its mass, presses against the walls of the pouch 32(a). Also, gravity forces the pouch 32(a) to open by stretching the accordion-shaped folds on the side walls of the pouch 32(a). This opening action of the accordion-shaped pouch 32(a) is shown in FIG. 2B. Specifically, as the bodily waste 40 enters the pouch 32(a) though opening 37, the mass of the bodily waste 40 opens the pouch 32(a) by stretching the accordion-shaped folds into flatter walls.

The ends of the side walls 36 can be more rigid than the side walls 36 so as to provide definition to the opening 37 of the pouch 32(a). This rigidity can facilitate the closing mechanism described below by providing a structure that can be pressed close by the closing mechanism. For example, more rigidity can be provided in the ends of the side walls 36 through the inclusion of a wire (e.g., a metal wire, a plastic wire, a rubber wire, etc.) attached to the ends.

Although shown folded in accordion-shaped folds, the pouch 32(a) can be folded in any manner so as to leave an opening for the receipt of bodily waste into the inner cavity of the pouch.

B. Pouch Opening Mechanisms

In another embodiment, the pouch can be closed, or substantially closed, in the absorbent article prior to donning by the wearer. In this embodiment, the pouch can be configured to open only upon contact with a liquid, such as urine or runny fecal matter. Thus, the pouch can remain substantially closed during use prior to an insult by the wearer.

Figure 3A:
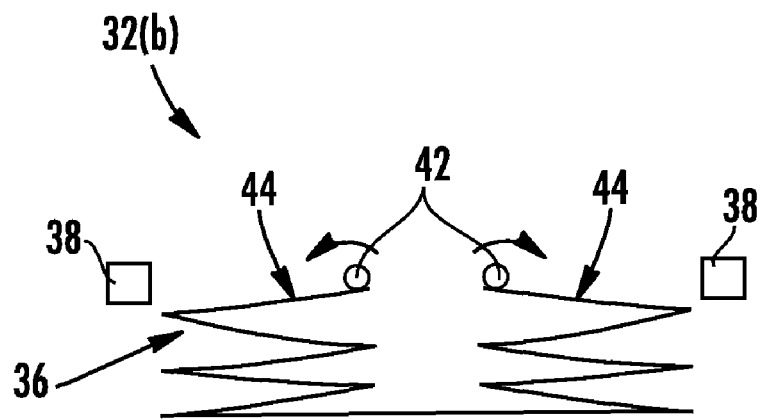
FIGS. 3A-3C sequentially show a process of a pouch opening upon wetting, collecting fecal matter, and then closing upon collection of the fecal matter in an absorbent article from a side, cut-away view.
Figure 3B:
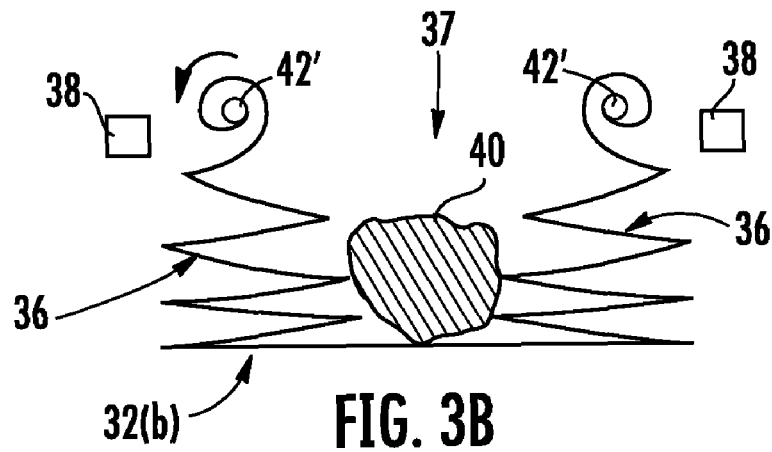
Figure 3C:
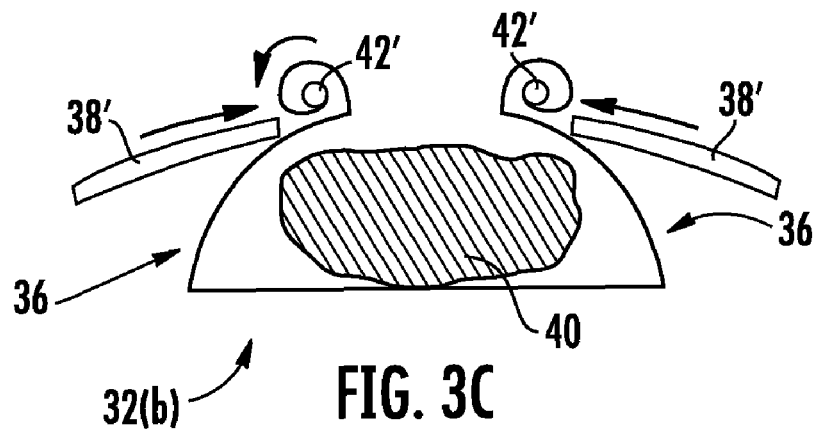
Figure 4A:
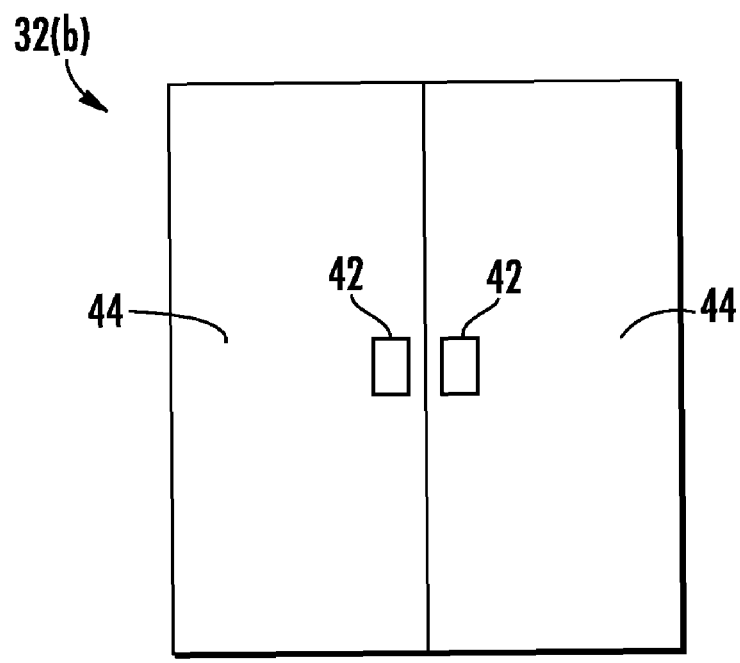

FIGS. 3A-3B and 4A depict exemplary embodiments of one particular pouch opening mechanism externally positioned relative to the pouch cavity. A pouch 32(b) is showing having the opening 37 substantially closed by the top pouch layer 44. A twisted, compressed substrate 42 is located on the ends adjacent the opening 37 of each top pouch layer 44 of the pouch 32(b). Upon wetting, the twisted, compressed substrate 42 expands from its compressed state. During its expansion, the twisted, compressed substrate 42 also unwinds from its twisted state. This unwinding provides a mechanism for opening the pouch 32(b) by expanding the opening 37 formed between the top pouch layers 44. Thus, upon insult by a bodily fluid, the pouch 32(b) can collect and retain the bodily waste 40 within the inner cavity of the pouch 37(b).

In this embodiment, a twisted, compressed substrate 42 having a cylindrical shape is positioned on the top pouch layer 44 adjacent to the opening 37. The twisted, compressed substrate 42 is laid on its side, such that a side of the twisted, compressed substrate 42 can be positioned for attachment to the top pouch layer 44. Specifically, the cylindrically shaped twisted, compressed substrate 42 can be laid sideways on the top pouch layer 44. A side of the twisted, compressed substrate 42 can then be attached to top pouch layer 44 adjacent to the opening 37 of the pouch 32(b).

Figure 4B:
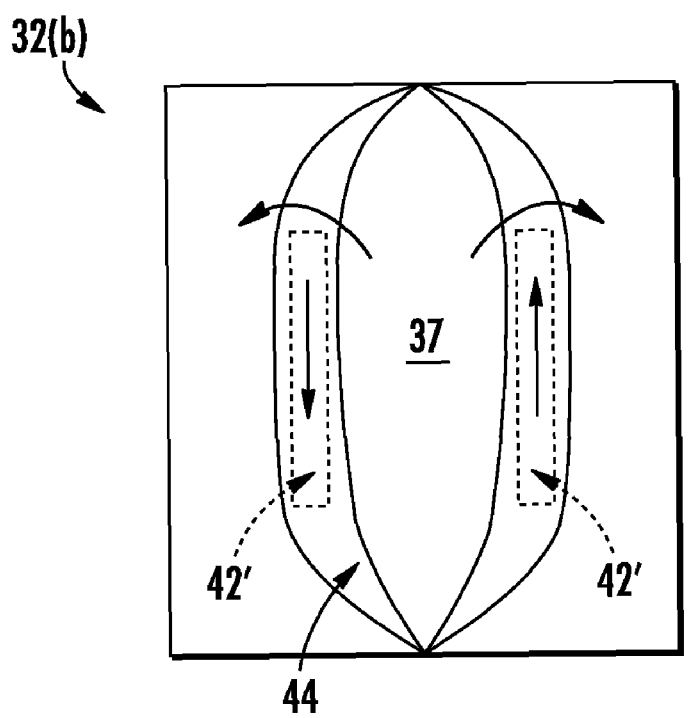

Upon wetting with a liquid, the twisted, compressed substrate 42 expands in the z-direction and unwinds from its twisted state. As it expands and unwinds, the twisted, compressed substrate 42 rolls away from the opening 37. The pouch 32(b) opens by expanding the opening 37 due to the rolling of each twisted, compressed substrate 42, as shown in FIGS. 3B and 4B. This rolling opens the pouch 32(b) by winding the top pouch layer 44 around the expanded, unwound twisted, compressed substrate 42' to widen the opening 37 of the pouch 32(b). Thus, bodily waste 40 can be collected by the pouch 32(b).

Attaching the twisted, compressed substrate 42 to the top pouch layer 44 can be achieved using any suitable method. In one particular embodiment, the twisted, compressed substrate 42 can be adhered to the top pouch layer 44 through the use of an adhesive.

In an alternative embodiment, the pouch opening can be opened through a pouch opening mechanism positioned within the pouch cavity (e.g., internally positioned relative to the pouch). For example, referring to FIGS. 9A and 9B, a pouch 32(c) is shown having twisted, compressed substrates 42 located within the inner cavity of pouch 32(c). In this embodiment, one end of the twisted, compressed substrate 42 is attached (e.g., adhered) to the inner, cavity facing surface of the top pouch layer 44 adjacent to the opening 37. In addition, the opposite end of the twisted, compressed substrate 42 can optionally be attached to the bottom surface of the pouch 32(c).

Upon wetting, the twisted, compressed substrate 42 expands in the z-direction and unwinds from its twisted state. This combination of expansion and unwinding causes the opening 37 to widen, while simultaneously increasing the area of the inner cavity available for collecting bodily waste. Once expanded, the expanded, unwound twisted, compressed substrate 42' also gives structural support to the inner cavity of the pouch 32(c) to facilitate the collection and retention of bodily waste.

Figure 9A:
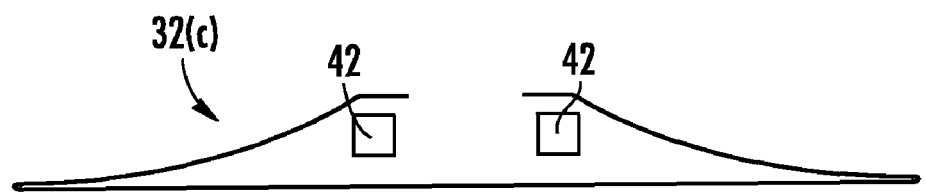
FIGS. 9A and 9B show an exemplary pouch having an expanding interior area utilizing expanding compressed substrates.
Figure 9B:
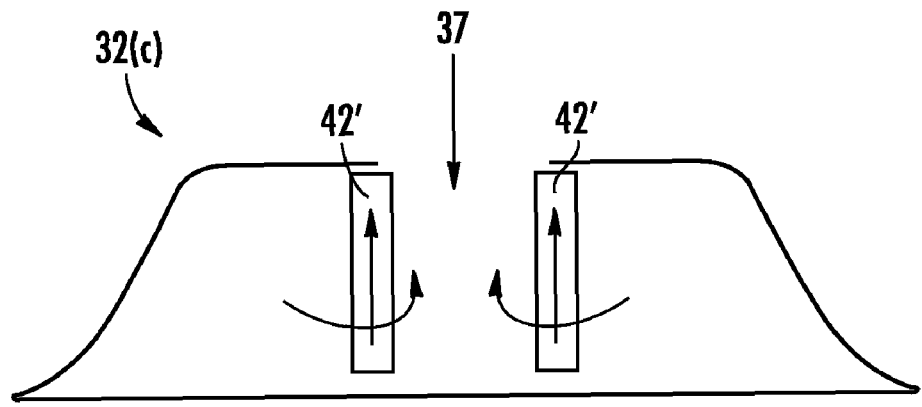

Although shown utilizing two twisted, compressed substrates 42, any number of twisted, compressed substrates 42 can be utilized within the cavity of the pouch 32(c). For example, from 2 to 10 twisted, compressed substrates 42 can be positioned within the inner cavity of the pouch 32(b) as shown in FIGS. 9A and 9B. The use of the internally positioned twisted, compressed substrates with the pouch can be with an open pouch or with a pouch having a pouch opening mechanism.

The twisted, compressed substrate 42 can be, in one embodiment, constructed from a highly compressed web material. In order to provide the unwinding action upon wetting, the substrate is not only compressed in the z-direction, but also twisted either before or during compression.

The twisted, compressed substrate 42 is formed by compression-molding of the web material and is configured to expand only in the direction of the compression forces (i.e., only in the z-direction) upon wetting. Thus, the direction of expansion upon contact with a liquid can be predisposed, allowing the direction of expansion of the twisted, compressed substrate to be predetermined when included as a pouch opening mechanism.

Figure 5A:
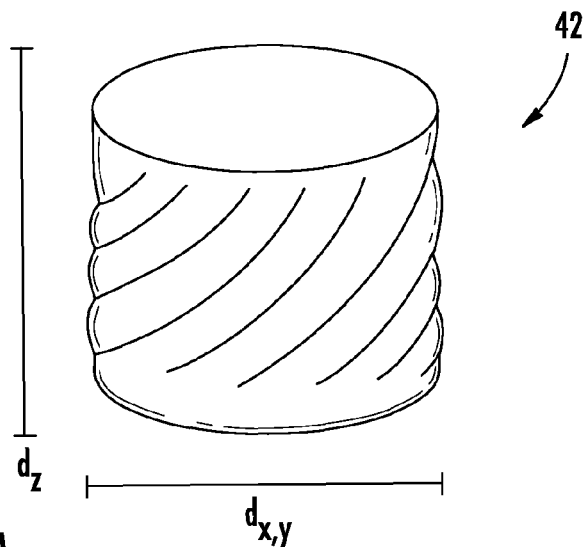
FIG. 5A shows an exemplary twisted, compressed substrate in its compressed state.
Figure 5B:
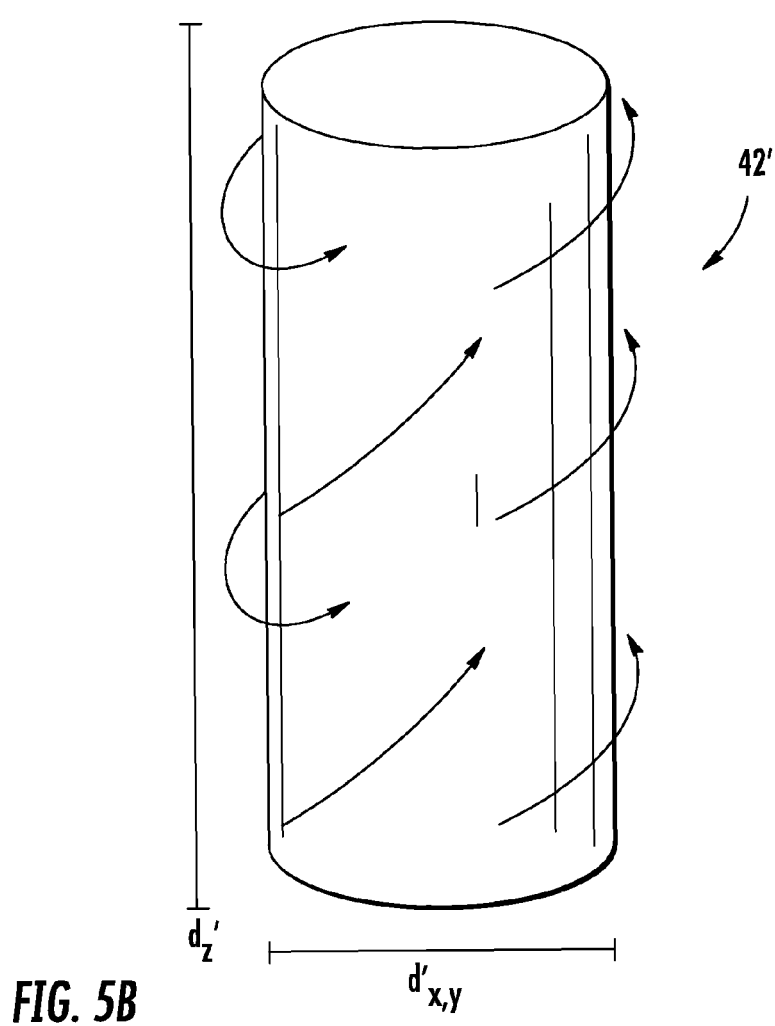
FIG. 5B shows the exemplary twisted, compressed substrate of FIG. 4A in its expanded state.

Referring to FIG. 5A, an exemplary twisted, compressed substrate 42 is shown in its dry, compressed state. The twisted, compressed substrate 42 has a compressed height $d_z$ in its z-direction while still in its dry state. Upon contact with a liquid, the twisted, compressed substrate 42 expands and unwinds to be an expanded twisted, compressed substrate 42' having an expanded height $d_z'$ (as shown in FIG. 5B). The degree of expansion in the z-direction can be predetermined by the type of material included within the twisted, compressed substrate 42 and the force asserted in forming the twisted, compressed substrate 42.

The expansion of the twisted, compressed substrate 42 is substantially 1-dimensional. Upon contact with a liquid expansion of the twisted, compressed substrate 42 occurs in the z-direction, without substantially increasing the size of the twisted, compressed substrate 42 in either the x-direction or y-direction. For example, referring to FIGS. 5A and 5B, the twisted, compressed substrate 42 is shown having a cylindrical shape, such that its size in the x- and y-directions are substantially equal (i.e., the diameter of the cylindrical twisted, compressed substrate 42). The diameter $d_{x,y}$ of the twisted, compressed substrate 42 remains substantially unchanged after contact with a liquid causing expansion in the z-direction. Thus, the diameter $d_{x,y}'$ of the expanded twisted, compressed substrate 42' shown in FIG. 1B is nearly identical to the diameter $d_{x,y}$ of the twisted, compressed substrate 42 shown in FIG. 1A (e.g., $d_{x,y}' \leq 1.1$ times $d_{x,y}$).

The expansion of the twisted, compressed substrate can be stated as an "expansion ratio" comparing of the degree of expansion in the z-direction compared to the degree of expansion in both the x- and y-directions (i.e., $d_z'$ divided by $d_z$ compared to $d_{x,y}'$ divided by $d_{x,y}$). In particular embodiments, the twisted, compressed substrate can expand more than about 2:1.1 in the z-direction compared to the x- and y-directions, such as greater than 3:1.1, and from about 5:1.1 to about 10:1.1. For example, the expansion ration can be greater than about 2:1.05, such as greater than about 3:1.05, such as from about 5:1.05 to about 10:1.05.

For example, the twisted, compressed substrate 42 suitably expands to at least about 2 times its original height $d_z$ in the z-direction when dry (i.e., expands 200%), and more suitably it expands to at least about 3 times the original height $d_z$ when dry (i.e., expands 300%). For example, in some embodiments, the expanded twisted, compressed substrate 42' can have a thickness or height $d_z'$ that is from about 5 times to about 10 times its original height $d_z$ (i.e., expands from about 500% to about 1000%).

In one particular embodiment, the diameter $d_{x,y}'$ of the expanded twisted, compressed substrate 42' can be less than about 110% of the diameter $d_{x,y}$ of the twisted, compressed substrate 42 in a dry state (i.e., less than about 1.1 times the original diameter $d_{x,y}$), such as from 100% (i.e., unchanged in diameter upon contact with a liquid in the x- and y-directions) to about 107% (i.e., about 1.07 times the original diameter $d_{x,y}$). For instance, the diameter $d_{x,y}'$ of the expanded twisted, compressed substrate 42' can be from about 100.5% to about 105% of the diameter $d_{x,y}$ of the twisted, compressed substrate 42 in a dry state.

Of course, the twisted, compressed substrate 42 can be molded into any other shape, including but not limited to cuboids, cubes, cones, etc. No matter the particular shape of the twisted, compressed substrate 42, the dimensions in the x- and y-directions do not substantially increase upon contact with a liquid.

The twisted, compressed substrate 42 is configured to expand to the expanded twisted, compressed substrate 42' nearly immediately upon contact with a small amount of a liquid. For example, the 1-dimensional expansion can occur within about 10 seconds of the twisted, compressed substrate 42 contacting a liquid, such expanding in less than about 5 seconds. In some embodiments, the 1-dimensional expansion of the twisted, compressed substrate 42 can occur from about 1 second to about 5 seconds, such as from about 1 second to about 3 seconds. Thus, the pouch 32 can be opened nearly immediately upon the first insult of the absorbent article.

In order to initiate the expansion of the twisted, compressed substrate 42, the twisted, compressed substrate 42 is configured to expand upon contact with a small amount of liquid. This amount of liquid need not completely saturate the twisted, compressed substrate 42. Of course, the amount of liquid necessary to cause complete expansion of the twisted, compressed substrate 42 to the expanded twisted, compressed substrate 42' can vary with the size of the twisted, compressed substrate 42. However, when used in an absorbent article, the twisted, compressed substrate 42 is configured, in most embodiments, to expand upon contact with greater than about 0.1 milliliters (mL), such as from about 0.5 mL to about 7 mL, and from about 1 mL to about 5 mL. At these liquid levels, the twisted, compressed substrate 42 can at least double in height in the z-direction with an expansion ratio of at least 2:1.1, as stated above.

The twisted, compressed substrate offer the moisture triggered z-directional expansion with a significant amount of energy. Specifically, the twisted, compressed substrate can expand in the z-direction with an exerted force up to about 16 pounds per square inch (psi), such from about 10 psi to about 15 psi.

The web material that is compressed to form the twisted, compressed substrate can be a nonwoven web of fibers. Although the particular type of fiber is not a limitation of the invention, some fibers are particularly suitable for forming the twisted, compressed substrate 42 to be included within an absorbent article. The fibers may be, for example, any combination of synthetic or pulp fibers. The selected average fiber length and denier will generally depend on a variety of factors and desired processing steps.

In one embodiment, a substantial portion of the fibers may be cellulosic pulp staple fibers. Pulp fibers may be utilized to reduce costs, as well as impart other benefits to the twisted, compressed substrate 42, such as improved absorbency. Some examples of suitable cellulosic fiber sources include virgin wood fibers, such as thermomechanical, bleached and unbleached pulp fibers. Pulp fibers may have a high-average fiber length, a low-average fiber length, or mixtures of the same. Some examples of suitable high-average length pulp fibers include northern softwood, southern softwood, redwood, red cedar, hemlock, pine (e.g., southern pines), spruce (e.g., black spruce), combinations thereof, and so forth. Some examples of suitable low-average fiber length pulp fibers may include certain virgin hardwood pulps and secondary (i.e. recycled) fiber pulp from sources such as, for example, newsprint, reclaimed paperboard, and office waste. Hardwood fibers, such as eucalyptus, maple, birch, aspen, and so forth, may also be used as low-average length pulp fibers. These pulp fibers can be formed into a nonwoven web (e.g., a tissue web) according to any process (e.g., wetlaid, airlaid, bonded carded process, etc.).

In one particular embodiment, the web is a non-woven web of rayon material. In particular, the rayon material can be manufactured by a spun lace method in which a web is formed out of viscose rayon and fibers are coupled using a high-pressure water stream.

Alternatively, a majority of the fibers of the nonwoven web may be formed from synthetic polymers. Synthetic fibers can be formed into nonwoven fabrics or webs from many processes such as for example, meltblowing processes, spunbonding processes, bonded carded web processes, etc.

"Meltblown fibers" refers to fibers formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

"Spunbonded fibers" refers to small diameter substantially continuous fibers that are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Petersen, U.S. Pat. No. 3,542,615 to Dobo, et al., and U.S. Pat. No. 5,382,400 to Pike et al., which are incorporated herein in their entirety by reference thereto for all purposes. Spunbond fibers are generally not tacky when they are deposited onto a collecting surface. Spunbond fibers can sometimes have diameters less than about 40 microns, and are often between about 5 to about 20 microns.

Exemplary synthetic polymers for use in forming nonwoven web may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. If desired such as those described above, may also be employed. It should be noted that the polymer(s) may also contain other additives, such as processing aids or treatment compositions to impart desired properties to the fibers, residual amounts of solvents, pigments or colorants, and so forth.

Monocomponent and/or multicomponent fibers may be used to form the nonwoven web. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack, et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,277,976 to Hogle, et al., U.S. Pat. No. 5,162,074 to Hills U.S. Pat. No. 5,466,410 to Hills, U.S. Pat. No. 5,069,970 to Largman, et al., and U.S. Pat. No. 5,057,368 to Largman, et al., which are incorporated herein in their entirety by reference thereto for all purposes.

Although any combination of polymers may be used, the polymers of the multicomponent fibers are typically made from thermoplastic materials with different glass transition or melting temperatures where a first component (e.g., sheath) melts at a temperature lower than a second component (e.g., core). Softening or melting of the first polymer component of the multicomponent fiber allows the multicomponent fibers to form a tacky skeletal structure, which upon cooling, stabilizes the fibrous structure. For example, the multicomponent fibers may have from about 5% to about 80%, and in some embodiments, from about 10% to about 60% by weight of the low melting polymer. Further, the multicomponent fibers may have from about 95% to about 20%, and in some embodiments, from about 90% to about 40%, by weight of the high melting polymer. Some examples of known sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del.

Fibers of any desired length may be employed, such as staple fibers, continuous fibers, etc. In one particular embodiment, for example, staple fibers may be used that have a fiber length in the range of from about 1 to about 150 millimeters, in some embodiments from about 5 to about 50 millimeters, in some embodiments from about 10 to about 40 millimeters, and in some embodiments, from about 10 to about 25 millimeters. Although not required, carding techniques may be employed to form fibrous layers with staple fibers as is well known in the art. For example, fibers may be formed into a carded web by placing bales of the fibers into a picker that separates the fibers. Next, the fibers are sent through a combing or carding unit that further breaks apart and aligns the fibers in the machine direction so as to form a machine direction-oriented fibrous nonwoven web. The carded web may then be bonded using known techniques to form a bonded carded nonwoven web.

If desired, the nonwoven web may have a multi-layer structure. The other layers can be other nonwoven webs, films, and the like. For example, in one embodiment, at least two nonwoven webs can be combined to form a nonwoven laminate. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., which are incorporated herein in their entirety by reference thereto for all purposes. In addition, commercially available SMS laminates may be obtained from Kimberly-Clark Corporation under the designations Spunguard® and Evolution®.

Another example of a multi-layered structure is a spunbond web produced on a multiple spin bank machine in which a spin bank deposits fibers over a layer of fibers deposited from a previous spin bank. Such an individual spunbond nonwoven web may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven web may be provided as two or more individually produced layers of a spunbond web, a carded web, etc., which have been bonded together to form the nonwoven web. These individually produced layers may differ in terms of production method, basis weight, composition, and fibers as discussed above.

A nonwoven web constructed from synthetic fibers may also contain an additional fibrous component such that it is considered a composite. For example, a nonwoven web may be entangled with another fibrous component using any of a variety of entanglement techniques known in the art (e.g., hydraulic, air, mechanical, etc.). In one embodiment, the nonwoven web is integrally entangled with cellulosic fibers using hydraulic entanglement. Hydraulically entangled nonwoven webs of staple length and continuous fibers are disclosed, for example, in U.S. Pat. No. 3,494,821 to Evans and U.S. Pat. No. 4,144,370 to Boulton, which are incorporated herein in their entirety by reference thereto for all purposes. Hydraulically entangled composite nonwoven webs of a continuous fiber nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes.

No matter the particular construction of the nonwoven web, the web is compression molded into a twisted, compressed substrate 42 configured to expand 1-dimensionally. The 1-dimensional expansion generally occurs in the direction of the compression forces exerted during the formation of the twisted, compressed substrate 42. Thus, one of ordinary skill in the art would be able to form a twisted, compressed substrate 42 having any desired shape and any desired expansion parameters. Additionally, the web is twisted either prior to or during compression.

Figure 6:
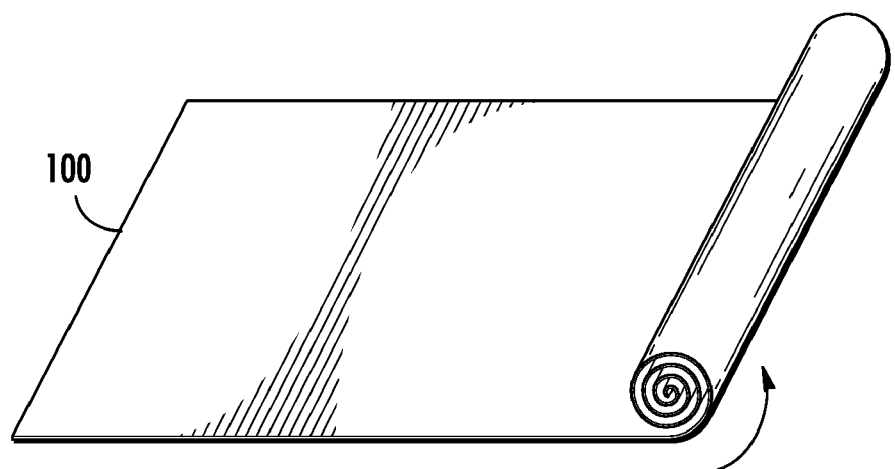
FIGS. 6 and 7 show an exemplary process of rolling and twisting a nonwoven substrate to create a twisted compressed substrate.
Figure 7:
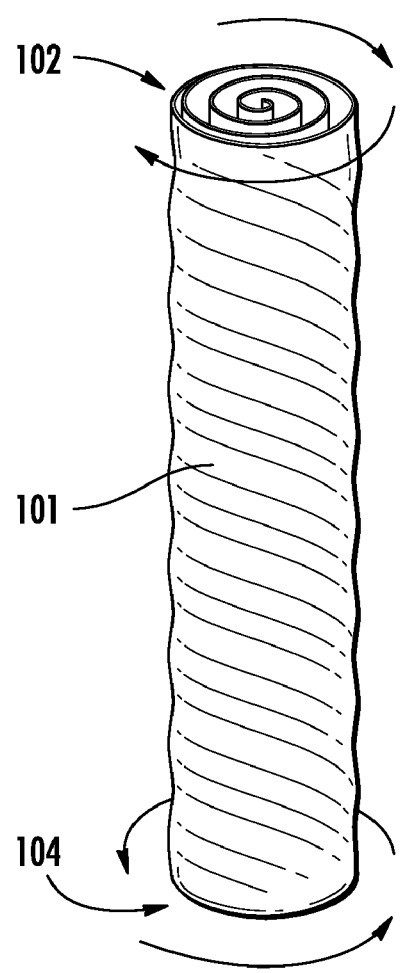

In one embodiment, the compressed web materials can be formed by first folding or rolling the web material into a tube-like shape, such that the web material is generally longer in the z-direction than in the x- and y-directions. For example, FIG. 6 shows a web material 100 being rolled into a cylindrical tube. This folded or rolled web material can then be twisted along its length. Referring to FIG. 7, the top section 102 of the rolled cylindrical tube 101 of web material 100 is twisted in a direction opposite to the bottom section 104. The amount of twist in the rolled cylindrical tube 101 can be measured as the relative amount of twist between the top section 102 and the bottom section 104. The amount of twisting can vary depending on the amount of unwinding desired. In one embodiment, the web material can be twisted at least about 360° (i.e., the top section 102 is rotated at least once relative to the bottom section), such as at least about 540°. In some embodiments, the web material can be twisted at least about 720°, such as from about 1080° to about 1800°.

In one particular embodiment, the web can be wetted (e.g., saturated with a liquid, such as water), twisted the desired amount, and then dried. Drying the web in is in a twisted state holds the web in its twisted state, such that the twisted, rolled web can be placed into a compression barrel without significantly unwinding before compression can begin.

The twisted material can then be placed into an elongated barrel such that the longer z-direction of the twisted web is parallel with the length of the barrel. The shape of the barrel in the x- and y-directions corresponds to the shape of the resulting twisted, compressed substrate 42. For example, to make the twisted, compressed substrate 42 shown in FIG. 5A, the barrel shape is cyclical such that the x- and y-directions of the barrel define a circle (or oval). Alternatively, the barrel shape can define any desired shape in the x- and y-directions to produce the twisted, compressed substrate 42 in the desired shape.

After placement in the barrel, the folded or rolled web is subjected to a compression force in a direction of the elongation of the barrel (i.e., the z-direction). This compression force is sufficient to compress the folded or rolled web into a twisted, compressed substrate 42 that will retain its initial shape until exposure to a liquid. That is, the disposable tissue should be subjected to compression molding under a pressure within a predetermined pressure range that varies according to the shape, configuration, and chemical construction of the web as described above. However, if the web is pressed under a pressure within the predetermined pressure range, it is compressed at a compressibility ($\Delta V/V$) in a range of 0.4 to 0.6. Here, the compressibility ($\Delta V/V$) represents a ratio of the amount of volume change ($\Delta V$) in the twisted, compressed substrate 42 to the volume (V) of the uncompressed web. The amount of volume change means the difference between the volume (V) of the uncompressed web and the volume of the twisted, compressed substrate 42.

For example, when making a twisted, compressed substrate 42 shaped as in FIG. 5A with a diameter $d_{x,y}$ of about 2 cm and a height $d_z$ of about 1 cm from a web. The web can have any initial size, such as less than about 20 cm×20 cm, such as from about 5 cm×5 cm to about 15 cm×15 cm. In one particular embodiment, the web can have an initial size of about 10×10 cm. The compression force can be apply a pressure to the folded or rolled tissue web of about 95 kiloNewton (kN) to about 300 kN, such as from about 145 kN to about 250 kN. In one particular embodiment the compression force can be from about 190 kN to about 200 kN in the z-direction.

Although the apparatus for forming the twisted, compressed substrate 42 can vary, a particularly suitable apparatus can include a cylindrical molding barrel having a longitudinal, through passage. The molding barrel can be supported on a table such that both end portions of the through passage of the molding barrel are exposed to the outside. An upper press can be installed vertically movably above the table and having a pressing rod to be inserted into the through passage of the molding barrel when the upper press moves downwardly. A lower press can also be installed vertically movably below the table and having a supporting rod to be inserted into the through passage of the molding barrel when the lower press moves upwardly.

In this set up, the upper press can include a power source for pressing the folded or rolled web received in the through passage. The supporting rod of the lower press closes an entrance of the through passage of the molding barrel to compression-mold the folded or rolled web and opens the entrance of the through passage to discharge the twisted, compressed substrate 42 from the through passage. The twisted, compressed substrate 42 is molded to have a shape that is the same as a space defined by the through passage of the molding barrel, the supporting rod of the lower press, and the pressing rod of the upper press. In a state where the entrance of the through passage of the molding barrel is opened, the twisted, compressed substrate 42 is discharged from the through passage by the upper press moving downwardly.

In one particular embodiment, the twisted, compressed substrate can be made with the compression molding apparatus and methods described in International Publication No. WO 200/082448 A1 Lee, et al., the disclosure of which is incorporated herein by reference.

Alternatively, the compression force can add a twisting component. For example, when using a cylindrical barrel, the pressing rod and the elongated barrel can be threaded such that that pressing rod twists while compressing the web material. In this embodiment, the pressing rod can have a web material contacting surface that engages the web material and twists it during compression.

Suitable twisted, compressed substrates are disclosed in U.S. patent application Ser. No. 12/129,795 filed on May 30, 2008, the disclosure of which is incorporated herein by reference.

II. Pouch Closing Mechanisms

After an insult of the absorbent article has occurred and the bodily fluid has been collected by the pouch, the pouch can be closed to inhibit release of the bodily fluid and/or fecal matter from the pouch.

The pouch closing mechanism can be, in one embodiment, a closing substrate (e.g., a twisted, compressed substrate as disclosed above or a compressed substrate without any substantial twisting). At least two closing substrates 38 can be positioned on either side of the pouch 32, as shown in FIGS. 1-4, with one closing substrate 38 positioned on either side of the pouch 32. The closing substrates are configured to expand upon contact with a liquid. As such, once the pouch 32 fills with the bodily waste 40, any excess bodily fluid can wet the closing substrate 38 causing its expansion. This expansion, in turn, closes the opening 37 of the pouch 32.

Figure 8A:
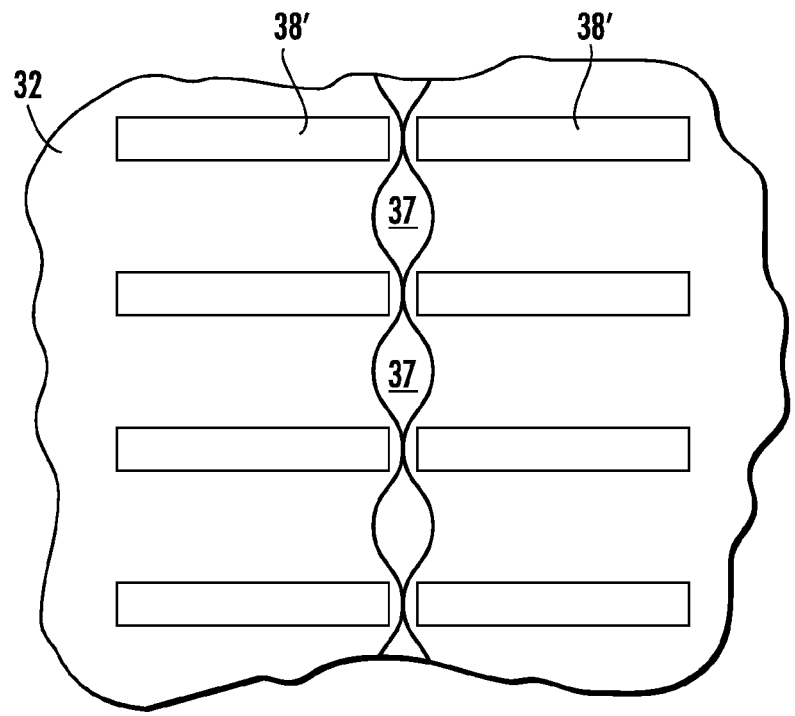
FIGS. 8A and 8B show exemplary embodiments of closing mechanisms utilizing a plurality of expanding compressed substrates.

Although FIGS. 1-4 show only a single closing substrate 38 on either side of the opening 37 of pouch 32, any number of closing substrates 38 can be utilized to form the closing mechanism. For example, referring to FIGS. 8A and 8B, a plurality of closing substrates 38 can be utilized to close the opening 37. In the exemplary embodiment of FIG. 8A, a plurality of closing substrates 38 are aligned (i.e., positioned opposite each other) such that upon expansion the closing substrates 38 expand towards each other. Once fully expanded, the ends of the closing substrates 38 contact each other to close the opening 37.

Figure 8B:
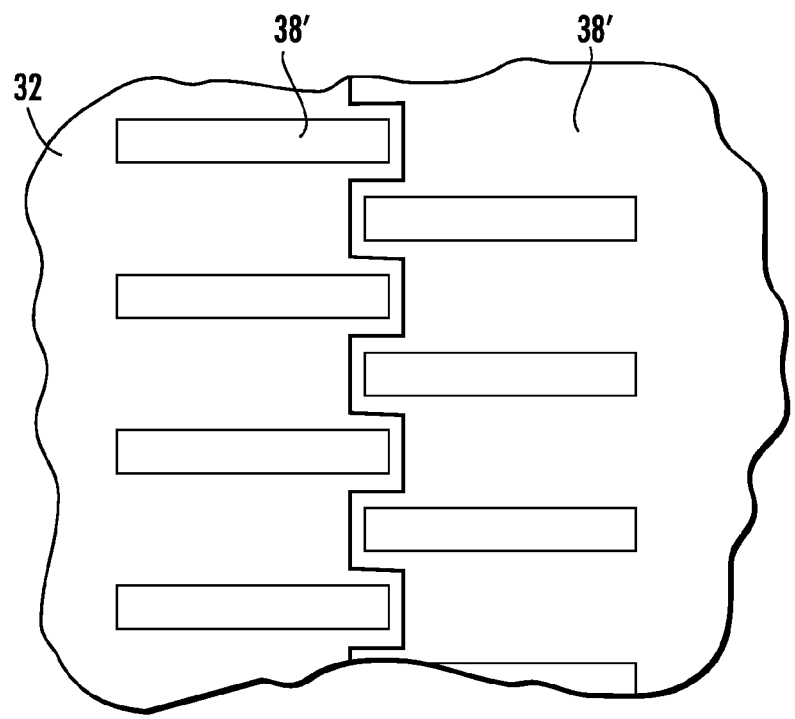

In the alternative embodiment, such as shown in FIG. 8B, a plurality of closing substrates 38 can be positioned opposite each other such that upon expansion the closing substrates 38 expand towards each other. However, in this embodiment, the closing substrates on opposite sides of each other are staggered, such that once fully expanded, the ends of the closing substrates 38 do not contact each other to close, but rather form a staggered fitting closing the opening 37.

The closing substrates 38 can be attached (e.g., adhered) to the edge of the top pouch layer 44 adjacent to the opening 37. Thus, upon expansion, the closing substrates 38 forces the opening 37 closed. However, attachment is not necessary when the edges of the top pouch layer 44 adjacent the opening 37 are sufficiently rigid to allow for the closing substrate 38 to function.

In operation, there is not an essential need for any unwinding action of the closing substrates during expansion. Thus, in one particular embodiment, the closing substrates are compressed substrates that expand substantially in the z-direction. For example, suitable compressed substrates are disclosed in U.S. patent application Ser. Nos. 11/955,916 and 11/955,937 filed on Dec. 13, 2007, the disclosures of which are incorporated in their entirety herein. Such compressed substrates can be essentially made as described above, simply without the twisting step in the process.

EXAMPLES

Example 1

A sheet of polyethylene film (12 cm×20 cm) was folded in order that the ends were brought to the center to form a slit. The edges were folded back away from the slit measuring 4 mm. At the center was placed a 8 mm compressed spunlace compressed substrate (8 mm diameter×6 mm height), and the ends of the compressed substrate had the film edges glued to the opposite ends. The slit now measured 6 mm. When the compressed substrate was wet with water the compressed substrate expanded in the z-direction twisting as it decompressed. The result was that the slit was opened and the gap enlarged due to the opposite sides were slightly rotated up or down by the compressed substrate (25 mm at the widest and 15 mm at the narrowest). The walls were 30 mm at the highest and 15 mm at the lowest. This illustrates the method of opening a flap or pouch within an absorbent article driven by moisture such as urine, menses or feces.

Example 2

A square sheet (12 cm×12 cm) of polyethylene film was folded in half. At the edges was placed an 8 mm compressed spunlace substrate. The top and bottom of the cylindrical substrate was glued (superglue) to the films edges. This gave the gap between the pouch measuring 8 mm. When the compressed substrate was wet with water the pill expanded in the z-direction twisting as it grew. This resulted in the pouch opening to 30 mm at the narrowest and 50 mm at the highest and was clearly twisted in opening as the edges were moved away from each other in the opening process.

Example 3

A square sheet (12 cm×12 cm) of polyethylene film had an 8 mm compressed spunlace substrate placed at its edge and glued with superglue on its side with the film covering half of its cylinder surface. Thus, the film was rolled partly around the side of the cylinder. When the compressed substrate was wet with water it expanded with twisting action it rolled the polyethylene film around the expanding compressed substrate resulting in the film rolling up like carpet. This demonstrates the mechanism of a pouch or flap can be made to open by having these compressed substrates placed along the end of the slit of the pouch or flap and rolling open when coming in contact with moisture.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. An absorbent article comprising
   a liquid-permeable body-side liner;
   a liquid-impermeable outer cover;
   an absorbent core positioned between the liquid-permeable body-side liner and the liquid-impermeable outer cover;
   a pouch positioned between the liquid-permeable body-side liner and the absorbent core, wherein the pouch is configured to collect and retain bodily waste through an opening facing the liquid-permeable body-side liner; and
   a closing mechanism comprising at least one compressed substrate having a cylindrical shape and being formed by compressing a rolled nonwoven web in a first direction, wherein the compressed substrate is positioned adjacent the pouch such that upon contact with a liquid, and wherein the compressed substrate expands 1-dimensionally in the first direction to close the pouch, the compressed substrate having an expansion ratio of greater than 3:1.1.

2. An absorbent article as in claim 1, wherein the pouch is constructed of a liquid-impermeable film.

3. An absorbent article as in claim 1, wherein the pouch is folded such that the opening is configured to receive bodily waste without the use of a pouch opening mechanism.

4. An absorbent article as in claim 3, wherein the pouch comprises side walls having at least one accordion-shaped fold.

5. An absorbent article as in claim 3, wherein the pouch comprises side walls having an end adjacent to the opening, wherein the end of each side wall is more rigid than the side walls of the pouch.

6. An absorbent article as in claim 4, wherein the pouch comprises a wire at the end of each side wall.

7. An absorbent article as in claim 1 further comprising
   a first twisted, compressed substrate attached to an external surface of a top pouch layer and adjacent to the opening of the pouch, wherein the first twisted, compressed substrate is positioned such that upon contact with a liquid, the first twisted, compressed substrate expands and unwinds causing the first twisted, compressed substrate to wind the top pouch layer about the first twisted, compressed substrate to expand the opening.

8. An absorbent article as in claim 7, wherein a second twisted, compressed substrate is attached to an external surface of a top pouch layer opposite the opening of the pouch as the first twisted, compressed substrate.

9. An absorbent article as in claim 7, wherein the first twisted, compressed substrate defines a cylindrical shape having an angled body between two ends, and wherein the angled body is attached to the external surface of the top pouch layer.

10. An absorbent article as in claim 1, wherein the pouch comprises at least one twisted, compressed substrate positioned internally within the pouch.

11. An absorbent article as in claim 10, wherein the twisted, compressed substrate is attached to an internal surface of the pouch along a bottom layer.

12. An absorbent article as in claim 10, wherein the twisted, compressed substrate is attached to an internal surface of a top pouch layer.

13. An absorbent article as in claim 10, wherein the pouch comprises from 2 to 6 compressed substrates positioned internally within the pouch.

14. An absorbent article as in claim 1, wherein the closing mechanism comprises a plurality of compressed substrates.

15. An absorbent article as in claim 14, wherein the plurality of compressed substrates are arranged such that a first portion of the compressed substrates are positioned on one side of the opening of the pouch and a second portion of the compressed substrates are positioned on an opposite side of the opening.

16. An absorbent article as in claim 15, wherein the first portion of the compressed substrates and the second portion of the compressed substrates are substantially aligned across the opening from each other.

17. An absorbent article as in claim 15, wherein the first portion of the compressed substrates and the second portion of the compressed substrates are substantially staggered across the opening from each other.

18. An absorbent article as in claim 1, wherein the pouch is positioned within a crotch region of the absorbent article.

19. The absorbent article as in claim 1, wherein the nonwoven web comprises rayon fibers.

20. The absorbent article as in claim 1, wherein the compressed substrate has an expansion ratio of about 5:1.05 to about 10:1.05.

* * * * *

UNITED STATES PATENT AND TRADEMARK OFFICE
CERTIFICATE OF CORRECTION

| | | |
|---|---|---|
| PATENT NO. | : 8,324,445 B2 | Page 1 of 1 |
| APPLICATION NO. | : 12/164426 | |
| DATED | : December 4, 2012 | |
| INVENTOR(S) | : John Gavin MacDonald et al. | |

It is certified that error appears in the above-identified patent and that said Letters Patent is hereby corrected as shown below:

In the claims,

Column 19, Line 16, before "the compressed substrate" and after "liquid" ", and wherein" should be deleted.

Signed and Sealed this
Fourteenth Day of April, 2015

Michelle K. Lee
*Director of the United States Patent and Trademark Office*